(12) United States Patent
Klawun et al.

(10) Patent No.: US 8,606,534 B2
(45) Date of Patent: Dec. 10, 2013

(54) METHOD FOR QUANTIFYING PEAKS IN AN ANALYTICAL SIGNAL

(75) Inventors: Christoph Klawun, Bartlesville, OK (US); Aosheng Wang, Eden Prairies, MN (US)

(73) Assignee: Siemens Aktiengesellschaft, Munich (DE)

( * ) Notice: Subject to any disclaimer, the term of this patent is extended or adjusted under 35 U.S.C. 154(b) by 365 days.

(21) Appl. No.: 13/155,172

(22) Filed: Jun. 7, 2011

(65) Prior Publication Data

US 2012/0143547 A1    Jun. 7, 2012

(30) Foreign Application Priority Data

Jun. 7, 2010    (EP) ..................................... 10165057

(51) Int. Cl.
*G01R 13/00*    (2006.01)
*G06F 17/18*    (2006.01)

(52) U.S. Cl.
USPC ............. 702/66; 702/179; 702/182; 702/189; 702/190

(58) Field of Classification Search
USPC ...................................... 702/66–70, 179–190
See application file for complete search history.

(56) References Cited

PUBLICATIONS

Yang et al. (hereinafter "Yang") "Comparison of Public Peak Detection Algorithms for MALDI Mass Spectrometry Data Analysis", BMC Bioinformatics, Biomed Central, London, GB, vol. 10. No. 1, Jan 6, 2009.*

Vach et al. (hereinafter "Vach") "Peak Detection in Mass Spectrometry Data using Repeated Measurements—A Graphical Approach", pp. 1-17, Oct. 1, 2006.*

Vach et al. "Peak Detection in Mass Spectrometry Data using Repeated Measurements—A Graphical Approach", pp. 1-17, Oct. 1, 2006.

Yang et al. "Comparison of Public Peak Detection Algorithms for MALDI Mass Spectrometry Data Analysis", BMC Bioinformatics, Biomed Central, London, GB, vol. 10. No. 1, Jan. 6, 2009.

* cited by examiner

*Primary Examiner* — Phuong Huynh
(74) *Attorney, Agent, or Firm* — Cozen O'Connor

(57) ABSTRACT

A method for quantifying peaks in an analytical signal, peaks in the analytical signal being quantified by recording successive signal values and applying a peak analysis methodology to the recorded successive signal values within an interval to obtain a set of peak quantification results. Before the same peak analysis methodology is applied to the modified signal to quantify the peaks in the signal, random noise is added to the analytical signal and/or the signal is shifted within the interval to facilitate optimization of the parameters of the peak analysis methodology and to improve the robustness of the method in runtime applications. A subsequent statistical evaluation of the peak quantification results from the multiple repeated peak analyses of the original and modified signals is used to detect an occurrence of and to reduce the chance of a possible error in the peak quantification that needs to be alarmed or addressed.

7 Claims, 3 Drawing Sheets

METHOD FOR QUANTIFYING PEAKS IN AN ANALYTICAL SIGNAL

BACKGROUND OF THE INVENTION

1. Field of the Invention

The present invention relates to a computer-based method for quantifying peaks in an analytical signal by recording successive signal values of the analytical signal and applying a peak analysis methodology to the recorded successive signal values within an interval for obtaining a set of peak quantification results. The interval may contain all signal values or the signal values of a portion of interest of the recorded analytical signal.

2. Description of the Related Art

The majority of conventional peak analysis algorithms commonly used for quantification of peaks (i.e., peak areas or peak heights) in analytical signals, such as chromatograms or spectra, are based on derivatives of the analytical signals. These derivatives of the analytical signals are inherently sensitive to noise and signal shifts, especially when low signal-to-noise ratio (S/N) signals are involved. Real peaks often have poor shapes, such as tailing, fronting, split peaks and/or shouldered peaks. Consequently, a peak analysis algorithm often requires optimization of a set of algorithm parameters to permit adaption of the algorithm to different peak shapes, which is also often sensitive to noise and shifts in a "raw" signal. Thus, the natural presence of noise and/or signal shifts in analytical signals often interferes with quantification of the peaks, which causes inaccurate, imprecise, and sometimes erroneous quantification of the analytes corresponding to these peaks.

In a laboratory environment, it may be feasible, albeit expensive or tedious, for an experienced user to manually inspect the results of peak quantification for serious errors caused by such interference. However, the consequence of this interference is often more serious in a continuous and unattended process monitoring environment, where erroneously reported results may require expensive manual inspections of the monitored process, and may result, for example, in inaccurate gas custody transfer billing, or may even cause the initiation of an erroneous emergency shutdown preparation of an entire process line.

This problem has only been partially solved by filtering out a portion of the noise prior to performing peak analysis. Conventional filtering methods merely include simple moving average, Savitzky-Golay smoothing, Gaussian filtering, Fourier transform filtering, and wavelet transform filtering.

SUMMARY OF THE INVENTION

It is therefore an object of the present invention to facilitate optimization of a peak quantification method including optimizing the parameters of a peak analysis methodology, thereby reducing the chance of quantification errors occurring when the optimized peak quantification method is used during subsequent calibration and sample analyses, and to improve runtime robustness in process monitoring.

This and other objects and advantages are achieved in accordance with the invention by implementing, in a computer, a method for quantifying peaks in an analytical signal by recording successive signal values of the analytical signal and applying a peak analysis methodology to the recorded successive signal values within an interval to obtain a set of peak quantification results.

Thus, before applying the peak analysis methodology to a modified signal to quantify the peaks in the signal, random noise is added to the analytical signal and/or the signal is shifted within an interval under consideration. The step sequence of noise addition and/or signal shift and peak quantification may be repeated multiple times with different noise and/or a different amount and/or direction of shift added or applied each time to the originally recorded signal. The noise-addition methodology and signal-shift methodology can be used either alone or together as needed. A subsequent statistical evaluation of the peak quantification results from the multiple repeated peak analyses of the original and modified signals is used to detect an occurrence of and to reduce a chance of a possible error in the peak quantification that needs to be alarmed or addressed.

Other objects and features of the present invention will become apparent from the following detailed description considered in conjunction with the accompanying drawings. It is to be understood, however, that the drawings are designed solely for purposes of illustration and not as a definition of the limits of the invention. It should be further understood that the drawings are not necessarily drawn to scale and that, unless otherwise indicated, they are merely intended to conceptually illustrate the structures and procedures described herein.

BRIEF DESCRIPTION OF THE DRAWINGS

The invention will now be described in further detail with reference to the following drawings, in which.

DETAILED DESCRIPTION OF THE PREFERRED EMBODIMENTS

Figure 1:
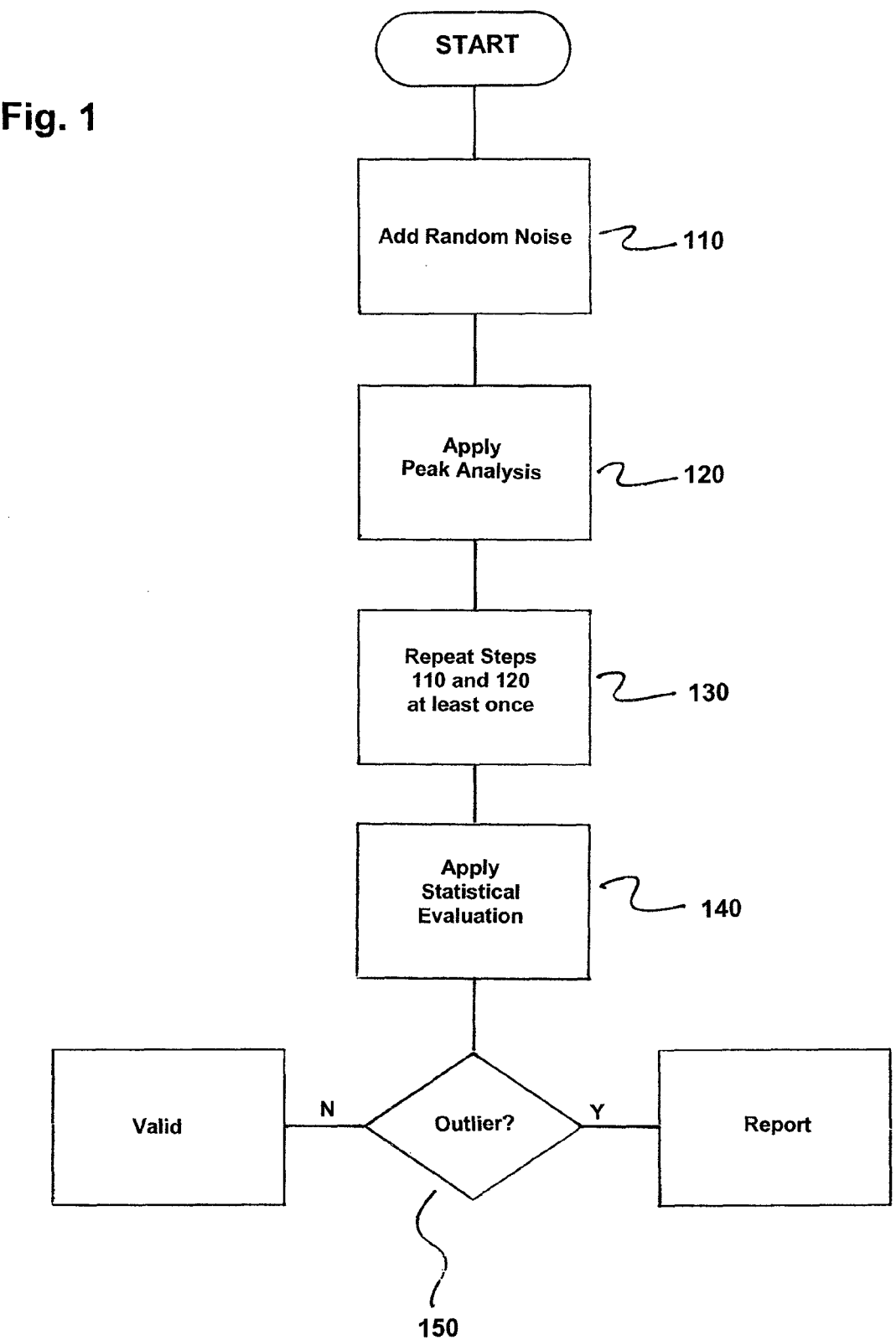
FIG. 1 is a flow chart of the method in accordance with an embodiment of the invention.

The method of the invention can be used during method development to define a more robust set of parameters to be used by a peak analysis methodology to reduce the chance of errors occurring during quantification of peaks in analytical signals. The method of the invention can also be used during subsequent calibration and sample analyses with the defined peak analysis parameters to further reduce the chance of errors, detect any such error that may occur, and thereby to improve the runtime robustness in the quantification of peaks.

The various following examples Ia, Ib, IIa, IIb and III provide exemplary descriptions of the method in accordance with the invention.

Example I

Repeated Peak Analyses of the Same Analytical Signal with Noise Additions

Example Ia

During Method Development

Step 1 Successive values of an analytical signal are acquired and recorded.

Step 2 A peak analysis methodology is applied to the recorded successive values of the analytical signal within an interval to quantify peaks in the analytical signal. Here, the interval may contain all signal values or only the signal values of a portion of interest of the recorded signal.

Step 3 Random noise is added to the recorded successive values of the analytical signal in the interval. The amount of noise may be similar to the signal-to-noise ratio (S/N) of the original signal, where the S/N may be estimated in Step 2.

Step 4 The peak analysis methodology is applied to random-noise-modified recorded successive signal values of the analytical signal of Step 3 to quantify peaks in the modified signal.

Step 5 Steps 3 and 4 are repeated at least once with different random noise added.

Step 6 A statistical evaluation methodology, such as Gubbs' test or Dixon's test, is applied to sets of peak quantification results obtained in Steps 2 and 4 to detect whether there is an outlier in the peak quantification results.

(a) Peak quantification results from Step 2 are accepted as valid results if there is no outlier.

(b) Peak quantification results from Step 2 are reported as invalid if there is at least one outlier, where the parameters of the peak analysis methodology are adjusted and a restart at Step 2 occurs.

Example Ib

During Unattended Runtime Quantification

Steps 1 to 5 are performed as described in Example Ia.

Step 6 A statistical evaluation methodology, such as Gubbs' test or Dixon's test, is applied to sets of peak quantification results obtained in Steps 2 and 4 to detect whether there is an outlier in the peak quantification results.

(a) Peak quantification results from Step 2 are accepted as valid results if there is no outlier.

(b) Peak quantification results from Step 2 are reported as valid, but a degree of certainty is reduced, if there is one outlier.

(c) Peak quantification results from Step 2 are reported as invalid if there is more than one outlier.

Example II

Repeated Peak Analyses of the Same Analytical Signal with Time Shifts

Example IIa

During Method Development

Step 1 Successive values of an analytical signal are acquired and recorded.

Step 2 A peak analysis methodology is applied to the recorded successive signal values of the analytical signal within an interval to quantify peaks in the signal. The interval may contain all signal values or only the signal values of a portion of interest of the recorded successive signal values of the analytical signal.

Step 3 The recorded successive signal values of the analytical signal within the interval are shifted by at least one position. Successive signal values of the analytical signal shifted out at one end of the interval are discarded. Positions vacated at the other end of the interval are filled with the original values of the analytical signal before the shift. Alternatively, and if the interval contains only the signal values of a portion of the recorded successive signal values of the analytical signal, neighboring signal values may be shifted in from outside into the interval.

Step 4 The peak analysis methodology is applied to the recorded successive signal values of the analytical signal in the interval to quantify peaks in the modified signal.

Step 5 Steps 3 and 4 are repeated at least once each time with a differing amount and/or direction of shift.

Step 6 A statistical evaluation methodology, such as Gubbs' test or Dixon's test, is applied to sets of peak quantification results obtained in Steps 2 and 4 to detect whether there is an outlier in the peak quantification results.

(a) Peak quantification results from Step 2 are accepted as valid results if there is no outlier.

(b) Peak quantification results from Step 2 are reported as invalid if there is at least one outlier. Parameters of the peak analysis methodology are adjusted and a restart at Step 2 occurs.

Example IIb

During Unattended Runtime Quantification

Steps 1 to 5 are performed in accordance with the above-described Example IIa.

Step 6 A statistical evaluation methodology, such as Gubbs' test or Dixon's test, is applied to sets of peak quantification results obtained in Steps 2 and 4 to detect whether there is an outlier in peak quantification results.

(a) Peak quantification results from Step 2 are accepted as valid results if there is no outlier.

(b) Peak quantification results from Step 2 are reported as valid, but the degree of certainty is reduced if there is one outlier.

(c) Peak quantification results from Step 2 are reported as invalid if there is more than one outlier.

Example III

Repeated Peak Analyses of the Same Analytical Signal with Noise Additions and Time Shifts Step 1 Successive values of an analytical signal are acquired and recorded.

Step 2 A peak analysis methodology is applied to the recorded successive signal values of the analytical signal within an interval to quantify peaks in the signal.

Step 3 Random noise is added to the signal values in the interval.

Step 4 The peak analysis methodology is applied to the signal values in the interval to quantify peaks in the random-noise modified recorded successive signal values of the analytical signal. Here, it should be noted that step 4 is optional and may be omitted.

Step 5 The successive signal values of the analytical signal within the interval are shifted by at least one position.

Step 6 The peak analysis methodology is applied to the successive signal values of the analytical signal in the interval to quantify peaks in the random-noise modified recorded successive signal values of the analytical signal.

Step 7 Repeating Steps 3 and 4 are repeated at least once and/or Steps 5 and 6 are repeated at least once with different noise or each time with a different amount and/or direction of shift.

Step 8 A statistical evaluation methodology, such as Gubbs' test or Dixon's test, is applied to sets of peak quantification results obtained in Steps 2, 4 and 6 to detect whether there is an outlier in the peak quantification results. The method is then continued in accordance with Step 6 of Example I or Example II.

FIG. 1 is a flow chart of the method in accordance with an embodiment of the invention. In accordance with the contemplated embodiment, the method is implemented in a computer for quantifying peaks in an analytical signal by recording successive signal values of the analytical signal and by applying a peak analysis methodology to the recorded successive signal values of the analytical signal within an interval to obtain a set of peak quantification results. The method comprises adding random noise to the recorded successive signal values of the analytical signal, as indicated in step 110.

The peak analysis methodology is applied in the computer to the random-noise-modified successive signal values of the analytical signal to obtain the set of peak quantification results, as indicated in step 120.

The step of adding the random noise and the step of applying the peak analysis methodology are repeated at least once, as indicated 130. Here, each random noise that is added to the recorded successive signal values of the analytical signal is different each time the step of adding is repeated.

A statistical evaluation methodology is applied in the computer to obtained sets of peak quantification results to check peak quantification results for outliers, as indicated in step 140.

Peak quantification results from the recorded successive signal values of the analytical signal are accepted in the computer as valid results if there is no outlier and the peak quantification results from the recorded successive signal values of the analytical signal are reported if there is at least one outlier, as indicated in step 150.

Figure 2:
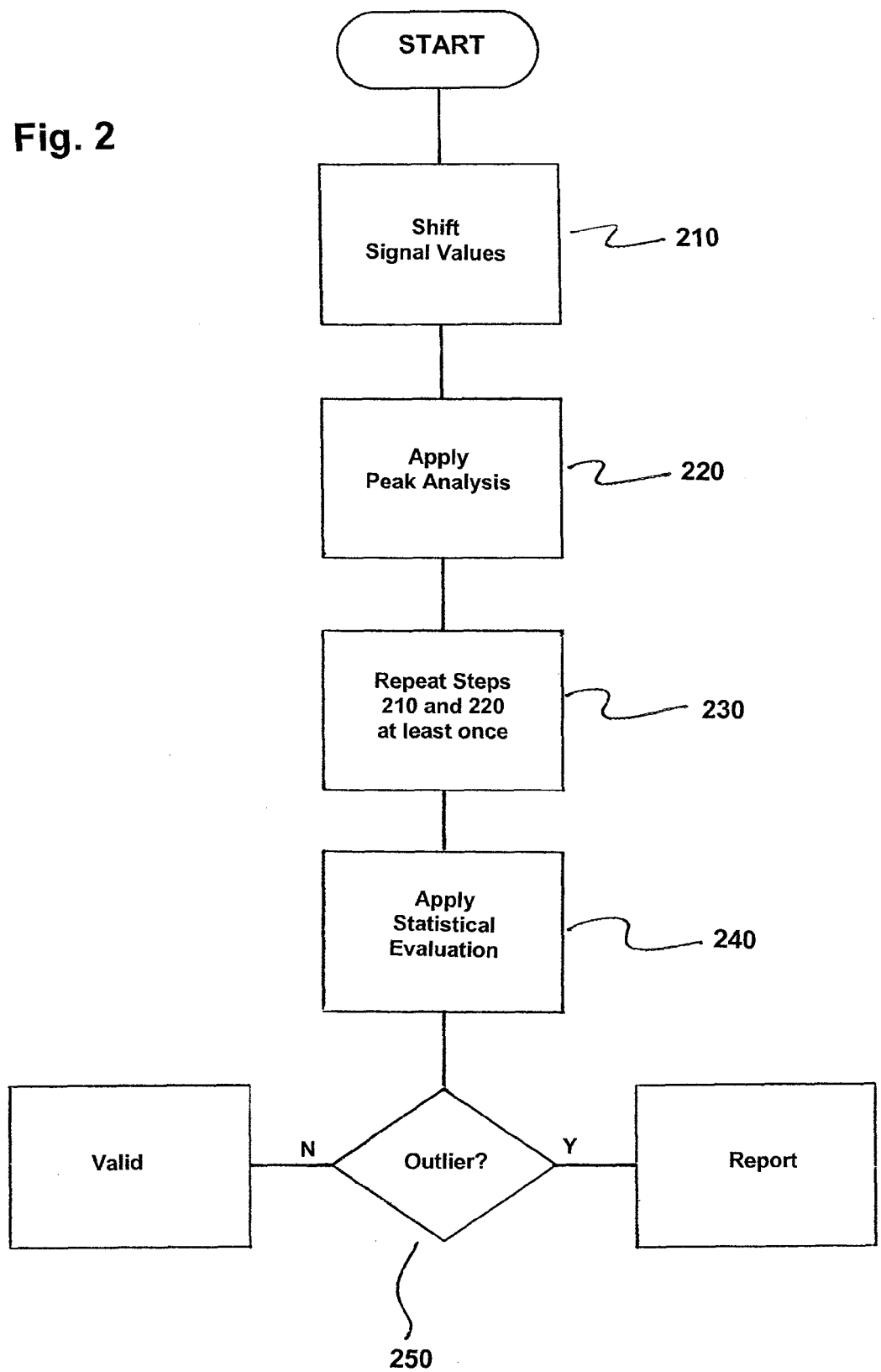
FIG. 2 is a flow chart of the method in accordance with an alternative embodiment of the invention.

FIG. 2 is a flow chart of the method in accordance with an alternative embodiment of the invention. In accordance with the contemplated embodiment, the method is implemented in a computer for quantifying peaks in an analytical signal by recording successive signal values of the analytical signal and by applying a peak analysis methodology to the recorded successive signal values of the analytical signal within an interval to obtain a set of peak quantification results. The method comprises shifting, in the computer, the recorded successive signal values of the analytical signal within the interval by at least one position, as indicated in step 210. Here, recorded successive signal values shifted out at one end of the interval are discarded and positions vacated at the other end of the interval are filled with original values before the shift or with neighboring signal values shifted from outside in the interval.

The peak analysis methodology is applied in the computer to the recorded successive signal values of the analytical signal in the interval to obtain the set of peak quantification results, as indicated in step 220.

The step of shifting the recorded successive signal values of the analytical signal and the step of applying the same peak analysis methodology are repeated at least once by the computer, as indicated 230. Here, at least one of an amount and direction of shift against originally recorded successive signal values of the analytical signal is different each time the step of shifting is repeated.

A statistical evaluation methodology is applied to the obtained sets of peak quantification results to check the sets of peak quantification results for outliers, as indicated 240.

The sets of peak quantification results from the recorded successive signal values of the analytical signal are accepted as valid results if there is no outlier and the peak quantification results from the recorded successive signal values of the signal are reported if there is at least one outlier, as indicated 250.

Figure 3:
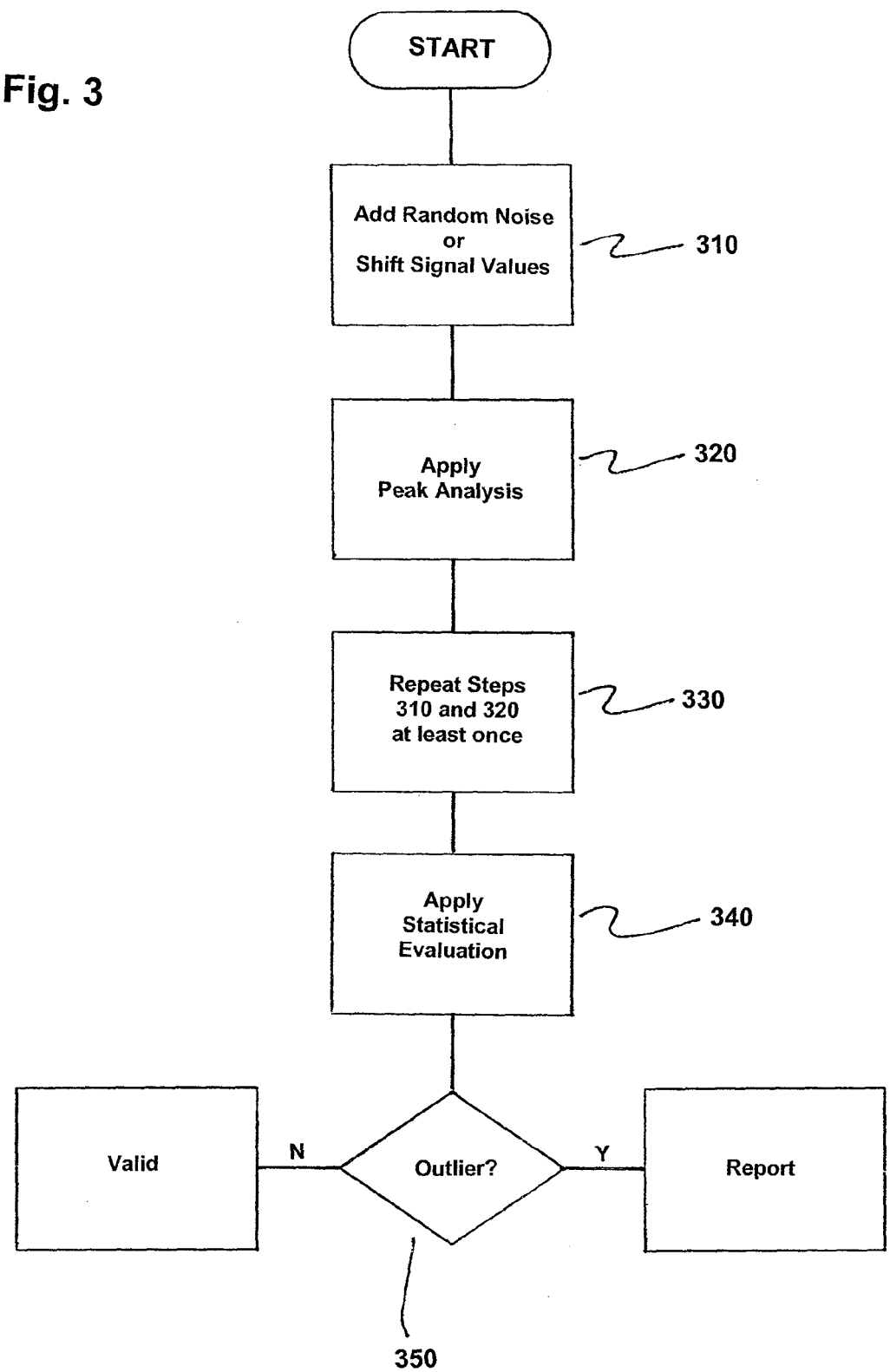
FIG. 3 is a flow chart of the method in accordance with an alternative embodiment of the invention.

FIG. 3 is a flow chart of the method in accordance with alternative embodiment of the invention. In accordance with the contemplated embodiment, the method is implemented in a computer for quantifying peaks in an analytical signal by recording successive signal values of the analytical signal and applying a peak analysis methodology to the signal values within an interval for obtaining a set of peak quantification results. The method comprises adding random noise to the recorded successive signal values of the analytical signal within the interval or shifting the recorded successive signal values of the analytical signal within the interval by at least one position, as indicated 310. Here, recorded successive signal values shifted out at one end of the interval are discarded and positions vacated at the other end of the interval are filled with originally recorded successive signal values before the shift or with neighboring signal values shifted from outside in the interval.

The peak analysis methodology is applied in the computer to the recorded successive signal values of the analytical signal values in the interval to obtain the set of peak quantification results, as indicated 320.

The step of adding the random noise or shifting the recorded successive signal values of the analytical signal and the step of applying the peak analysis methodology are repeated at least once to ensure that the steps of adding the random noise and shifting the recorded successive signal values of the analytical signal are each performed at least once, as indicated 330. Here, in cases in which the steps of adding random noise or shifting the signal values are performed at least twice, the random noise added to the recorded successive signal values of the analytical signal or at least one of an amount and direction of shift against the recorded successive signal values of the analytical signal is different each time the step of adding or shifting is repeated.

A statistical evaluation methodology is applied to the obtained sets of peak quantification results to check the peak quantification results for outliers, as indicated 340.

The peak quantification results from the recorded successive values of the analytical signal are accepted as valid results if there is no outlier and the peak quantification results from the recorded successive signal values of the analytical signal are reported if there is at least one outlier, as indicated 350.

Thus, while there have shown and described and pointed out fundamental novel features of the invention as applied to a preferred embodiment thereof, it will be understood that it is expressly intended that all combinations of those elements and/or method steps which perform substantially the same function in substantially the same way to achieve the same results are within the scope of the invention. Moreover, it should be recognized that method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A method, implemented in a computer, for quantifying peaks in an analytical signal by recording successive signal values of the analytical signal and applying a peak analysis methodology to the recorded successive signal values of the analytical signal within an interval to obtain a set of peak quantification results, the method comprising the steps of:

adding random noise to the recorded successive signal values of the analytical signal;

applying, in the computer, the peak analysis methodology to the random-noise-modified successive signal values of the analytical signal to obtain the set of peak quantification results;

repeating at least once the step of adding the random noise and the step of applying the peak analysis methodology, each random noise added to the recorded successive signal values of the analytical signal being different each time the step of adding is repeated;

applying, in the computer, a statistical evaluation methodology to obtained sets of peak quantification results to check peak quantification results for outliers; and accepting, in the computer, peak quantification results from the recorded successive signal values of the analytical signal as valid results if there is no outlier and reporting the peak quantification results from the recorded successive signal values of the analytical signal if there is at least one outlier.

2. The method of one claim 1, wherein the method is implemented during runtime of automated process analytics.

3. The method of claim 1, wherein parameters of the peak analysis algorithm are adjusted dependent on a number and amount of outliers.

4. A method, implemented in a computer, for quantifying peaks in an analytical signal by recording successive signal values of the analytical signal and applying a peak analysis methodology to the recorded successive signal values of the analytical signal within an interval to obtain a set of peak quantification results, the method comprising the steps of:

shifting, in the computer, the recorded successive signal values of the analytical signal within the interval by at least one position, recorded successive signal values shifted out at one end of the interval being discarded and positions vacated at the other end of the interval being filled with one of original values before the shift and neighboring signal values shifted from outside in the interval;

applying, in the computer, the peak analysis methodology to the recorded successive signal values of the analytical signal in the interval to obtain the set of peak quantification results;

repeating at least once the step of shifting, by the computer, the recorded successive signal values of the analytical signal and the step of applying the peak analysis methodology, at least one of an amount and direction of shift against originally recorded successive signal values of the analytical signal being different each time the step of shifting is repeated;

applying a statistical evaluation methodology to the obtained sets of peak quantification results to check the sets of peak quantification results for outliers; and accepting the sets of peak quantification results from the recorded successive signal values of the analytical signal as valid results if there is no outlier and reporting the peak quantification results from the recorded successive signal values of the signal if there is at least one outlier.

5. The method of one claim 4, wherein the method is implemented during runtime of automated process analytics.

6. A method, implemented in a computer, for quantifying peaks in an analytical signal by recording successive signal values of the analytical signal and applying a peak analysis methodology to the signal values within an interval for obtaining a set of peak quantification results, the method comprising the steps of:

adding random noise to the recorded successive signal values of the analytical signal within the interval or shifting the recorded successive signal values of the analytical signal within the interval by at least one position, recorded successive signal values shifted out at one end of the interval being discarded and positions vacated at the other end of the interval being filled with originally recorded successive signal values before the shift or neighboring signal values shifted from outside in the interval;

applying, in the computer, the peak analysis methodology to the recorded successive signal values of the analytical signal values in the interval to obtain a set of peak quantification results;

repeating at least once the step of adding the random noise or shifting the recorded successive signal values of the analytical signal and the step of applying the peak analysis methodology to ensure that the steps of adding the random noise and shifting the recorded successive signal values of the analytical signal are each performed at least once, in cases in which the steps of adding random noise or shifting the signal values are performed at least twice, the random noise added to the recorded successive signal values of the analytical signal or at least one of an amount and direction of shift against the recorded successive signal values of the analytical signal being different each time the step of adding or shifting is repeated;

applying a statistical evaluation methodology to the obtained sets of peak quantification results to check the peak quantification results for outliers; and accepting the peak quantification results from the recorded successive values of the analytical signal as valid results if there is no outlier and reporting the peak quantification results from the recorded successive signal values of the analytical signal if there is at least one outlier.

7. The method of one claim 6, wherein the method is implemented during runtime of automated process analytics.

* * * * *